United States Patent
Zheng et al.

(10) Patent No.: US 7,015,343 B2
(45) Date of Patent: Mar. 21, 2006

(54) SULPHONATED DEHYDROGENATED SYLVATE, THE PREPARATION AND USE

(75) Inventors: Liangyuan Zheng, Shanghai (CN); Shiwei Zhang, Beijing (CN); Li Zheng, Beijing (CN); Mingxin Wang, Beijing (CN); Yongli Zhao, Beijing (CN); Xuezhao Lu, deceased, late of Beijing (CN); Yongli Zhao, legal representative, Beijing (CN)

(73) Assignee: Shanghai Xingkang Pharmaceuticals Research & Development Co., Ltd., Shanghai (CN)

( * ) Notice: Subject to any disclaimer, the term of this patent is extended or adjusted under 35 U.S.C. 154(b) by 87 days.

(21) Appl. No.: 10/483,774

(22) PCT Filed: Jun. 4, 2002

(86) PCT No.: PCT/CN02/00387

§ 371 (c)(1), (2), (4) Date: Jan. 14, 2004

(87) PCT Pub. No.: WO03/093225

PCT Pub. Date: Nov. 13, 2003

(65) Prior Publication Data

US 2004/0162341 A1 Aug. 19, 2004

(30) Foreign Application Priority Data

Jul. 16, 2001 (CN) ................................ 01120289 A

(51) Int. Cl.
 C07F 9/94 (2006.01)
 C07F 3/06 (2006.01)
 A61K 31/19 (2006.01)

(52) U.S. Cl. .................. 556/78; 556/132; 514/569

(58) Field of Classification Search ............... 514/569; 556/78, 132
See application file for complete search history.

(56) References Cited

U.S. PATENT DOCUMENTS 4,529,602 A * 7/1985 Wada et al. ................. 514/569
5,830,913 A * 11/1998 Ogawa et al. ............... 514/569
6,730,702 B1 * 5/2004 Kono et al. .................. 514/569

FOREIGN PATENT DOCUMENTS

WO        WO 01/34143      *  5/2001

* cited by examiner

*Primary Examiner*—Porfirio Nazario-Gonzalez
(74) *Attorney, Agent, or Firm*—Andrews Kurth LLP

(57) ABSTRACT

This invention relates to salts of sulfodehydroabietic acid with bismuth or zinc, a kind of new salt useful in treating digestive canal ulcer, acute & chronic gastritis, and erosive gastritis etc., as well as its preparation and use. Said salts can be represented by formula (1), wherein R is $Bi(OH)^{++}$ or $Zn^{++}$, $2Bio^+$, $1/2ZnH$, n=0–10. The preparation method comprises following steps: (a) sequentially treating the industrial abietic acid calcium salt with acid, base and extracting with organic solvent to give abietic acid with less isomer; (b) reacting said abietic acid with Pd/C to provide dehydroabietic acid, then converting it to pure sulphonic product, namely sulfodehydroabietic acid, via sulphonation and recrystallization; (c) by use of neutralization or salt displacement reaction to convert the sulphonic product of zinc or bismuth salts of sulfodehydroabietic acid. The resultant salts can used to prepare medicine for treating digestive canal ulcer and gastritis.

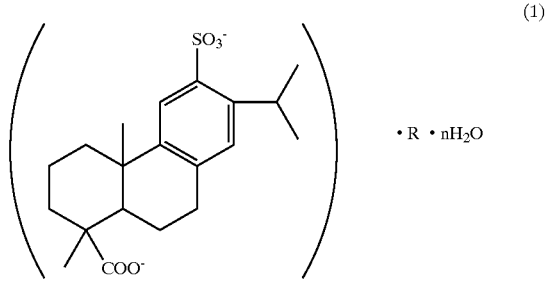

(1)

7 Claims, No Drawings

SULPHONATED DEHYDROGENATED SYLVATE, THE PREPARATION AND USE

TECHNICAL FIELD

This invention relates to salts of sulfodehydroabietic acid (chemical name: 1,4a-dimethyl-1-carboxyl-6-sulfo-7-isopropyl-1,2,3,4,4a,9,10,10a-octahydro-phenanthren e) with zinc or bismuth, the preparation thereof, the pharmaceutical composition containing said salts of sulfodehydroabietic acid with zinc or bismuth, and their use in preparing medication for treating digestive canal ulcer, acute and chronic gastritis, and erosive gastritis etc.

BACKGROUND TECHNOLOGY

Digestive canal ulcer and gastritis are related to excessive hydrochloric acid in gastric juice, pepsin activity, chemical damage and nerve tension, etc. The infection of *helicobacter pylori* is also an important factor. This kind of diseases is frequent, has a long course of disease, is not easily cured completely and costs highly. In clinic, this kind of diseases is generally treated by the method of using neutralizers such as calcium carbonate, aluminum hydroxide, blockers of histamine receptor like Ranitidine etc., inhibitors of ion pump like Omeprazole, protectors of ulcer surface like Sucralfate, carbenoxolone and salts of bismuth, or by the method of combining said medicines and antibiotics. However, the over use of traditional medicines for treating digestive canal ulcer like antacids will result in the reduce of hydrochloric acid in gastric juice, and thereby the digestion activity of pepsin is influenced obviously and indigestion is caused. In addition, the too high pH value will result in subsequent too much hydrochloric acid in gastric juice. The protector of ulcer surface like carbenoxolone has a function of adrenocorticohyperplasia, thereby, it will result in Sodium retention whose clinic symptoms are edema, higher blood pressure and lower blood potassium etc. Various antibiotics can strongly inhibit *helicobacter pylori* in vitro, but in clinic, even when applying antibiotics with medicine like inhibitors of ion pump together, the effect is not satisfactory either. One reason is that, most antibiotics are not stable under the acid condition in gastric juice, thereby, it is difficult to reach an effective treatment concentration on the surface of the gastric mucous membrane. The other reason is that medicine endurance will easily happen. Therefore, it is very difficult to cure the infection of *helicobacter pylori* completely even with the broadly recommended method of combination of medicines and antibiotics, and the disease is easy to reoccur. Moreover, once the disease reoccurs, the probability of digestive canal cancerization and other diseases increases.

Therefore, it is very necessary to further research and develop on new medicines of digestive canal ulcer.

Said sulfodehydroabietic acid in the present invention had been reported in 1930's as an intermediate for preparation of pure dehydroabietic acid. The derivation of said sulfodehydroabietic acid was reported as the detergent in 1970's. In 1980's, the research of TANABE SEIYAKU CO., LTD of Japan discovered that sulfodehydroabietic acid alkaline metal such as sodium, potassium and lithium salts, and alkaline earth metal such as calcium, magnesium and aluminum salts and various kinds of compositions containing nitrogen had obvious effects of protecting gastric mucous membrane, inhibiting the pepsin activity and killing *helicobacter pylori* without medicine endurance; therefore, they could be applied as treatment medicine for digestive canal ulcer and gastritis; meanwhile, after oral administration, this kind of medicine was mainly removed with dejecta, only a little was contained in urine, and no medicine was remained in the tissue, embryo and mother-milk of rats; thus, the toxic side effect was very weak.

In Chinese traditional medicine, rosin mainly contains abietic acid, abietic anhydride and various kinds of isomers of abietic acid. Therefore, the productivity of abietic acid is rather low by using traditional distilling method, and many isomers are contained which are difficult to remove. Therefore, a pure and single construct of dehydroabietic acid is very difficult to obtain after dehydrogenation by catalyzing and displacement. To obtain dehydroabietic acid, firstly, prepare sulfodehydroabietic acid which can be easily purifed; secondly, remove the sulfonic group by hydrolyzing, the productivity of distilling and preparing dehydroabietic acid being rather low (all less than 25%)

SUMMARY OF INVENTION

An object of the present invention is to provide salts of sulfodehydroabietic acid, wherein, said salts can be represented by formula (1):

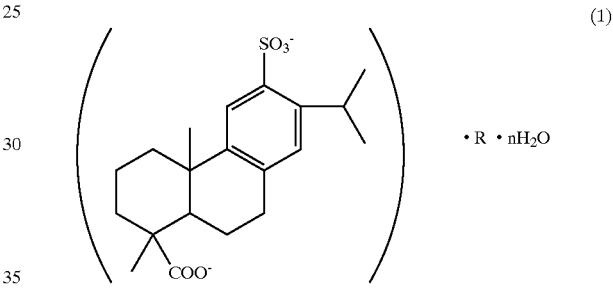

wherein, R is $Bi(OH)^{++}$, or $Zn^{++}$, or $2BiO^+$, $1/2ZnH$; n=0–10.

Another object of the present invention is to provide a method of preparing salts of sulfodehydroabietic acid represented by formula (1).

Another object of the present invention is to provide pharmaceutical composition containing salts of sulfodehydroabietic acid represented by formula (1) and their pharmaceutical excipient.

Another object of the present invention is to provide the use of salts of sulfodehydroabietic acid represented by formula (1) in preparing medicine useful for treating digestive canal ulcer, acute & chronic gastritis, and erosive gastritis etc.

DETAILED DESCRIPTION OF THE INVENTION

The aim of the present invention is to provide salts of sulfodehydroabietic acid, their preparation and use. Said salts of sulfodehydroabietic acid in the present invention can be used for treating digestive canal ulcer, acute & chronic gastritis, and erosive gastritis etc. With the method of the present invention to prepare salts of sulfodehydroabietic acid, the process is simple and the productivity is good.

To solve the technical problems mentioned above, the present invention adopts following technical scheme:

Salts of sulfodehydroabietic acid, said salts can be represented by formula (1):

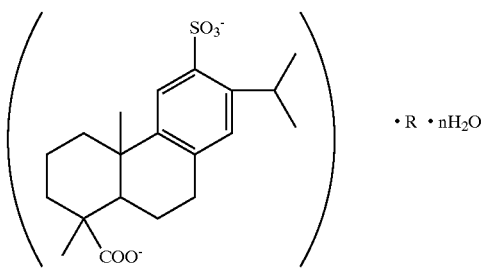

(1)

wherein, R is $Bi(OH(^{++}$, or $Zn^{++}$, or $2BiO^+$, $1/2ZnH$; n=0–10.

The method of preparing salts of sulfodehydroabietic acid of the present invention includes following steps:

(1) Mixing rosin and lime hydrate in the ratio (wt) of 1:0.1–1:1.5, stirring at 160–600° C. for 1–5 hours, to obtain solid abietic acid calcium salt;

(2) Dissolving said solid abietic acid calcium salt in $C_{1-6}$ fatty alcohol and $C_{1-6}$ fatty alcohol hydrous solution, or fatty acid ester, wherein the solvent used is 0.5–10 times as much as said solid abietic acid calcium salt, the unit ratio is ml/g; and adjusting pH value to 5–9 with mineral acid, so as to obtain abietic acid;

(3) Incubating said abietic acid at 200–300° C. for 1–5 hours with the catalyst of 0.1–5% (wt) of 5%–10% palladium/carbon, or incubating directly at 220–380° C. After incubation and cooling down, adding 0.5 to 10-fold (volume) solvent, said solvent can be any one of methanol, ethanol, propenol, acetyester acetic acid, benzene and methbenzene, keeping refluxed for 1–3 hours, filtering when it is warm, cooling down, allowing it to stand for overnight and be crystallized. Dehydroabietic acid is obtained after filtering.

(4) Adding said dehydroabietic acid into 1 to 10-fold (wt) 90–98% sulfuric acid pre-cooled to –20–20° C., after incubating for 0.5–10 hours with stirring, pouring it into ice cold water, wherein, said ice cold water is 5–50 times (wt) as much as said sulfuric acid. Then, lots of white precipitation is crystallized out. Filtering, washing the precipitates with water, and drying off. Dissolving the precipitates into 0.5 to 10-fold (wt) glacier acetic acid with heating, allowing the mixture to be cooled down and be crystallized. The sulfodehydroabietic acid is obtained after filtered and dried off.

Or, (5) Preparing single or double alkaline metal salts or alkaline earth metal salts of sulfodehydroabietic acid from said sulfodehydroabietic acid obtained with the conventional method.

(6) Preparing the salts of sulfodehydroabietic acid with bismuth or zinc, namely the composition represented by formula (1), based on the displacement reaction of single or double alkaline metal salts or alkaline earth metal salts of sulfodehydroabietic acid obtained from the previous steps with any one of zinc chloride, zinc sulfate, zinc nitrate, bismuth nitrate, bismuth subnitrate, and bismuth hydroxide in any one of solvents of $C_{1-6}$ fatty alcohol, water, DMF or DIMSO.

Or, (5)' Preparing the salts of sulfodehydroabietic acid with bismuth or zinc, namely the composition represented by formula (1), based on the neutralization reaction of sulfodehydroabietic acid obtained from the previous steps with any one of zinc oxide, zinc hydroxide, bismuth nitrate, bismuth subnitrate in any one of solvents of $C_{1-6}$ fatty alcohol, water, DMF or DIMSO.

The industrial abietic acid calcium salt adopted in the present invention is obtained by incubating rosin with lime hydrate at high temperature and then cooling down. In this reaction, rosin was first transformed into abietic acid calcium salt, so as to increase the productivity of the abietic acid in the next preparation step; meanwhile, high temperature makes isomers of abietic acid in rosin relocated for the first time, so as to decrease the content of isomers in abietic acid obtained. In fact, the abietic acid with single spectrum can be obtained based on the method of the present invention, then the pure dehydroabietic acid can be obtained based on direct dehydrogenation by catalyzing and displacement, where the preparation process is simple and the productivity is good (over 35%).

The use of salts of sulfodehydroabietic acid of the present invention, namely the use of the composition represented by formula (1), in preparing medicines for treating digestive canal ulcer, acute & chronic gastritis, and erosive gastritis etc.

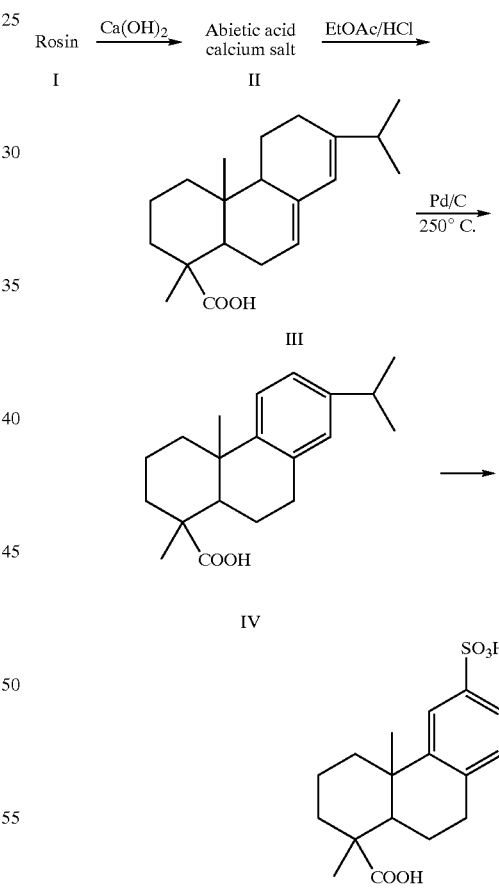

(1) Mixing rosin (I) and lime hydrate in the ratio (wt) of 1:0.1–1:1.5 with stirring at high temperature for 1–5 hours, then cooling down to obtain a light yellow and almost transparent solid abietic acid calcium salt (II).

Wherein, the ratio of rosin and lime hydrate is preferred to be 1:0.5. The reaction temperature should be controlled in the range of 160~600° C., and is preferred to be 200–300° C. The time for stirring is preferred to be 2–3 hours.

(2) Dissolving said abietic acid calcium salt (II) in proper solvent and adjusting pH to 5–9 with mineral acid. Filtering, allowing the filtered liquid to stand for overnight and be crystallized, then, abietic acid (III) is obtained after filtering.

Wherein, said solvent includes $C_{1-6}$ fatty alcohol and $C_{1-6}$ fatty alcohol hydrous solution, or fatty acid ester; the concentration of said $C_{1-6}$ fatty alcoholhydrous solution is 10–95% (wt). Methanol, ethanol and acetyester acetic acid are preferred. The amount of solvent used is 0.5–10 times (ml/g) as much as that of abietic acid calcium salt (II) used, and 1–5 times is more preferred. Said mineral acid includes hydrochloric acid, sulfuric acid, phosphoric acid and nitric acid, etc. In this invention, 90–98% (wt) hydrochloric acid is preferred, and the pH value is preferred to be 6–8.

The pure crystal abietic acid can be obtained based on re-crystallization, alternatively, it can be obtained based on direct dehydrogenation by catalyzing and displacement.

(3) The reaction of forming dehydroabietic acid (IV) from abietic acid (III) by displacement and dehydrogenation can be carried out under proper catalyst or under high temperature of 220–380° C. Adding proper catalyst can increase the ratio of displacement and dehydrogenation and shorten the reaction time. In the present invention, 0.1–5(wt) % of 5%–10% palladium/carbon is added, the reaction is at 200–300° C. for 1–5 hours, the solvent is added after cooling down, and after refluxed for 1–3 hours, the mixture is filtered when it is warm, then it is cooled down, standing for overnight and gets crystallized, then, dehydroabietic acid (IV) is obtained after filtered.

Wherein, the amount of catalyst is preferred to be 0.7–3%, and more preferred to be 2%. The proper solvents may be methanol, ethanol, propenol, acetyester acetic acid, benzene and methbenzene, wherein, ethanol is preferred. 10–95% (wt) ethanol hydrous solution may be used, the volume of solvents is 0.5–10 times as much as that of the abietitic acid (III), and preferably 1–3 times.

(4) Adding dehydroabietic acid (IV) obtained from the previous steps into 1 to 10-fold sulfuric acid pre-cooled to −20~20° C., incubating for 0.5–10 hours with stirring, pouring it into ice cold water, then, lots of white precipitation is crystallized Filtering, washing the precipitates with water, and drying off. Dissolving the precipitates into the glacier acetic acid with heating, allowing the mixture to be cooled down and be crystallized. The sulfodehydroabietic acid (V) is obtained after being filtered and dried off.

In the present invention, the sulfuration is carried out under −20~20° C., and preferably −10~10° C.; the preferred concentration of sulfuric acid is 98%; the amount of sulfuric acid used is 1 to 10-fold, and preferably 4 to 6-fold; the reaction time is 0.5–10 hours, preferably 1–2 hours; the amount of ice cold water is 5~50 times as much as that of the sulfuric acid, preferably 15~25 times; the amount of glacier acetic acid for re-crystallization is 0.5 to 10-fold, preferably 1.5 to 2.3-fold.

In the present invention, a method of preparing salts of sulfodehydroabietic acid with bismuth or zinc and their hydrous composition is also provided.

(1) The salts of sulfodehydroabietic acid with bismuth or zinc in the present invention can be obtained based on displacement reaction of single or double alkaline metal salts or alkaline earth metal salts of sulfodehydroabietic acid with bismuth salts or zinc salts in proper solvents.

Wherein, said single or double alkaline metal salts or alkaline earth metal salts of sulfodehydroabietic acid are composition without $H_2O$ or with crystal $H_2O$ of Na, K, Li, Mg or Ca, preferably, the composition without $H_2O$ or with crystal $H_2O$ of Na; said zinc salts used in the displacement reaction are referred to zinc chloride, zinc sulfate, zinc nitrate etc., said bismuth salt is referred to bismuth nitrate, bismuth subnitrate, and bismuth hydroxide; said proper solvent is referred to $C_{1-6}$ fatty alcohol, water, DMF or DMSO, preferably 0 to 100-fold water.

(2) The bismuth or zinc salts in the present invention can be obtained based on neutralization reaction of sulfodehydroabietic acid and any one of ZnO, $Zn(OH)_2$ or $Bi(NO_3)_2$ in proper solvent.

(3) The bismuth or zinc salts in the present invention can exist in the form without $H_2O$ or with crystal $H_2O$, and they are more stable with 1–8 crystal $H_2O$.

The medicine made from salts of sulfodehydroabietic acid for treating digestive canal ulcer and gastritis according to the present invention can be administered orally or non-orally, but the effect will be better in oral way. The matrix formulation for oral administration may be tablet, capsule, powder, granules and emulsion etc. Some medicine supplements and adjuvant such as adhibiter, correcter and diluter can be added into oral medicine.

The dosage of composition of the present invention is varied according to the age, weight and disease of the patients. It is generally 10–400 mg/kg per day, preferably, 40–130 mg/kg.

The composition of the present invention has no hormone functions, while has good functions of anti-ulceration, and has therapeutical and precautionary functions for gastric and digestive canal diseases such as digestive canal ulcer, gastritis, etc. Wherein, said digestive canal ulcer is referred to gastric ulcer and duodenal ulcer.

The present invention will now be further described by way of following experiments and examples of pathology and toxicology. It should be understood that these examples are merely for illustrative purposes and are not to be construed as limitations of the present invention.

EXAMPLES

Examples of Pathology and Toxicology

Example 1

The Inhibiting Effect of the Salts of Sulfodehydroabietic Acid with Zinc (NIPWZ) and Salts of Sulfodehydroabietic Acid with Bismuth (NIPWB) of the Present Invention on the Hydrochloric Acid in Gastric Juice and on the Pepsin Activity Wister rats (200–250 g), half were male and half were female, were starved for 48 hours and the pylori were ligated. Immediately after ligation, a suspension or solution of a salt in distilled water was administered orally into the stomachs in an amount of 2.0 ml/Kg; while 0.5% MC of the same volume was given to the control group. After administration of the test salt for 5 hours, the rats were killed. Their cardias were ligated and their stomachs were taken out. The gastric juice was collected into centrifuge tube and centrifuged at 2500 rpm for 10 min, the volume after residue removed was recorded as the total volume of the gastric juice. The acidity of gastric juice and pepsin activity were measured with the supernatant of the gastric juice after centrifuging.

(a) Measurement of the acidity of gastric juice: with 0.5 ml of gastric juice taken exactly, about 20 ml of distilled water added in, it was measured with pH meter. The mixture was titrated to pH 7 with 0.01 N NaOH solution, and the volume of 0.01 N NaOH solution used was recorded. Then, the volume (T.AC) was calculated corresponding to titrating to pH 7 with 0.01 N NaOH solution.

Acid concentration of gastric juice $(MEL) = (T.AC/2) \times 1000$

Total acid amount in gastric juice $(MEAH) = MEL \times$ (total volume of gastric juice/1000)

Inhibiting ratio on the secretion of gastric juice %=[(volume of the gastric juice of the control group−volume of the gastric juice of the treatment group)/volume of the gastric juice of the control group]×100%

Inhibiting ratio on the total acid amount in gastric juice %=[(MEAH of the control group−MEAH of the treatment group)/MEAH of the control group]×100%

(b) Enzyme assay for pepsin (Mett tube method): 0.5 ml of gastric juice was added exactly into a clean 50 ml flask with a plug, the flask was shaken to get a homogeneous solution, then, 15.0 ml of 0.05 N HCL solution was added in, in the meantime, two 3.0–4.0 cm long Mett tubes were put inside. The flask was plugged, shaken to get a homogeneous solution, left to stand at 37° C. for 24 hours. The length (mm) of the transparent part at the two ends of each Mett tube was measured precisely to get four values. The mean value was based on the four values, and the pepsin activity was calculated.

Inhibiting ratio of pepsin activity %=[(pepsin activity of the control group−pepsin activity of the treatment group)/pepsin activity of the control group]×100%

Test Result:

ratio for total acid amount is over 44%, the inhibiting ratio for pepsin activity is over 40%.

Example 2

Measurement of the Acute Toxicity of Salts of Sulfodehydroabietic Acid with Bismuth (NIPWB) for Oral Administration to Mice 20 second grade KunMing mice were provided, each weighing 20.1±1.3 g, 10 male and 10 female. Medicine was orally administered to them by twice with the maximal dose of 50 ml/Kg, the solvent was 0.5% MC. The abnormal reaction and the death after oral administration were recorded in details, observing was continued for 14 days, and the dead bodies were anatomized.

No abnormal reaction and death occurred during 14 days continuous observing after the oral administration of 8000 mg/Kg NIPWZ to mice ($LD_{50} \geq 8000$ mg/Kg).

Example 3

Measurement of the Acute Toxicity of Salts of Sulfodehydroabietic Acid with Zinc (NIPWZ) for Oral Administration to Mice 50 second grade KunMing mice were provided, each weighing 20.0±1.2 g, randomly divided into 5 groups, 10 for each group, 5 male and 5 female. Medicine was administered intra-gastrically by 40 ml/Kg once, the solvent was 0.5% MC. The doses for the 5 groups were: 4480 mg/Kg, 3000 mg/Kg, 2010 mg/Kg, 1350 mg/Kg, 910 mg/Kg, the ratio of any two abutted doses was 1:0.67. The abnormal

TABLE 1

Effect of oral administration of NIPWZ and NIPWB on gastric juice secretion of Pylorus-ligated rats (n = 8, X ± S)

| Group | Dose (mg/Kg) | Total volume of gastric juice (ml) | T.AC | MEL ($10^3$) | MEAH | activity of pepsin (U) |
|---|---|---|---|---|---|---|
| Control |  | 9.1 ± 3.2 | 6.42 ± 3.11 | 3.21 ± 1.56 | 29.3 ± 4.9 | 1.49 ± 0.30 |
| NIPWZ | 50 | 7.2 ± 2.9 | 3.83 ± 2.93 | 1.92 ± 1.47 | 13.8 ± 4.2** | 0.88 ± 0.33** |
|  | 100 | 7.0 ± 3.1 | 4.41 ± 2.64 | 2.21 ± 1.32 | 15.5 ± 4.1** | 0.66 ± 0.34 |
| NIPWB | 50 | 6.5 ± 2.5 | 4.85 ± 3.58 | 2.42 ± 1.79 | 15.9 ± 4.5** | 0.74 ± 0.61 |
|  | 100 | 7.6 ± 2.9 | 4.32 ± 3.30 | 2.16 ± 1.65 | 16.3 ± 4.7** | 0.36 ± 0.20** |

Note:
compared with the control group, \* P < 0.05, \*\* P < 0.01

TABLE 2

Inhibiting Effect of oral administration of NIPWZ and NIPWB on gastric juice secretion (n = 8, X ± S)

| Group | Dose (mg/Kg) | Inhibition to gastric juice secretion (%) | Inhibition ratio for total acid amount (%) | Inhibition ratio for pepsin activity (%) |
|---|---|---|---|---|
| Control | — | — | — | — |
| NIPWZ | 50 | 20.9 | 52.9 | 40.5 |
|  | 100 | 23.1 | 47.1 | 55.4 |
| NIPWB | 50 | 28.6 | 45.7 | 50.0 |
|  | 100 | 16.5 | 44.4 | 75.7 |

The salts of sulfodehydroabietic acid with bismuth or zinc have obvious inhibition effect (P<0.01) on total amount of hydrochloric acid of gastric juice and the pepsin activity when the treatment dose is 50–100 mg/Kg. The inhibition reaction and the death after oral administration were recorded in details, observing was continued for 14 days, and the dead bodies were anatomized. Wherein the $LD_{50}$ was determined by Bliss's method.

TABLE 3

Calculating half-death dose $LD_{50}$ (Bliss's method) after oral administration of NIPWZ.

| Dose | Loga-rithm | Number of mice | Death distribution | | | | Number of death | Ratio of death |
|---|---|---|---|---|---|---|---|---|
| mg/Kg | Dose X | unit | 2 h | 4 h | 24 h | 72 h | unit (F:M) | % |
| 4480 | 3.65 | 10 | 7 | 3 | 0 | 0 | 10 (5:5) | 100 |
| 3000 | 3.48 | 10 | 0 | 7 | 1 | 0 | 8 (5:3) | 80 |
| 2010 | 3.30 | 10 | 0 | 0 | 7 | 0 | 7 (5:2) | 70 |
| 1350 | 3.13 | 10 | 0 | 0 | 3 | 1 | 4 (1:3) | 40 |
| 910 | 2.96 | 10 | 0 | 0 | 0 | 0 | 0 (0:0) | 0 |

After oral administration of NIPWZ, $LD_{50}$=1728 mg/Kg, approximately 104 times as much as the clinic dose (taking 1000 mg/day for a 60 Kg human being).

EXAMPLES OF PREPARATION

Example 1

100 g of abietic acid and 50 g of lime hydrate were added into a 500 ml reaction bottle, heated to 350° C. and incubated for 2 hours. After the mixture naturally cooled down, the almost transparent solid abietic acid calcium salt was concreted, wherein, the softening point was 130–135° C.

Example 2

After it was ground, 700 g of abietic acid calcium salt was added into 600 of ml acetic ether and 90 ml of concentrated hydrochloric acid, the mixture was heated and refluxed for 10 min. The mixture was filtered after dissolved, allowed to stand still and be crystallized to give 140 g of abietic acid.

Mp. 162–166° C., $^1$HNMR(300 MHz, in $CDCl_3$, J in Hz) δ ppm: 7.430(1H, brs), 5.757(1H, brs), 5.332(1H, brs), 2.213(1H, seq.), 1.186(3H, s), 1.10(3H, d, J=7.2), 1.000(3H, d, J=7.2), 0.803(3H, s).

Example 3

115 g of abietic acid was put into a 1000 ml three-neck bottle, and then 2.3 g of 5% palladium/carbon catalyst was added in. The mixture was stirred at 250° C. (oil bath) for 2 hours, after slightly cooled down, 200 ml of 95% ethanol was added. The mixture was refluxed until completely dissolved, filtered when it was warm, allowed to stand still and to be crystallized to give 70 g of dehydroabietic acid after filtered and dried.

Mp. 168–170° C. $^1$HNMR (300 MHz, in $CDCl_3$, J in Hz) δ ppm: 7.167(1H, d, J=7.8), 7.005(1H, dd, J=1.2, 7.8), 6.886(1H, d, J=1.2), 2.904(2H, m), 2.822(1H, seq., J=7.2), 2.303(1H, brd, J=13.2), 2.245(1H, dd,J=2.0,13.2), 1.279 (3H, s), 1.221(6H, d, J=7.2), 1.215(3H, S).

Example 4

250 ml of concentrated sulfuric acid was added into a 1000 ml three-neck bottle cooled down to about −8° C. 50 g of ground solid dehydroabietic acid was added into said sulfuric acid with stirring. The stirring was kept for 1.5 hours after adding all of 50 g of solid dehydroabietic acid, then, 1000 ml of ice cold water was poured in slowly. The mixture was filtered after continuous stirring vigorously for 20 min, washed with appropriate amount of ice cold water until the filtered liquid becomes cloudy. The precipitates were transferred into a 500 ml three-neck bottle, ~200 ml glacier acetic acid was added in. The mixture was heated and refluxed, filtered, allowed to stand for overnight and be crystallized to give 37 g of sulfodehydroabietic acid after filtered and dried.

Mp. 210~215° C., $^1$HNMR(300 MHz, in $CDCl_3$, J in Hz) ppm: 7.839(1H, s); 7.058(1H, s); 7.058(1H, s), 3.985(1H, seq., J=6.9), 2.872(2H, dt), 2.373(1H, brd, J=12), 2.188(1H, dd, J=1.8, 12), 1.265(3H, s), 1.238(3H, d, J=6.9), 1.230(3H, d, J=6.9), 1.201(3H, s).

Example 5

40 g of sulfodehydroabietic acid was dissolved into 400 ml water, pH was 1–2. 8.4 g of NaOH was added with stirring, pH>10. 2 g of active carbon was added, filtered when it was warm after refluxed for 0.5 hours. The filtered solution was concentrated to 80 ml in vaccum, allowed to stand still and be crystallized, re-filtered. The precipitates were washed with 10 ml of water, air dried for 48 hours to give 35 g of sulfodehydroabietic acid disodium salt 8.5 $H_2O$ hydrate. Mp>300° C.

Example 6

5 g of sulfodehydroabietic acid was added into 100 ml water, and 1 g of ZnO was added. The mixture was heated to 90° C. and incubated for 15 min., filtered when it was warm. The precipitates were washed with 50 ml water and 50 ml 95% ethanol, dried at 60° C. for 48 hours to give 3.1 g of sulfodehydroabietic acid zinc salt 5 $H_2O$ hydrate.

Mp>300° C.; $IR^v_{max}$ (KBr): 3474, 3039, 2948, 2869, 1700, 1634, 1539, 1396, 1364, 1185, 1168, 1100, 1059, 1045, 1035, 1009, 977, 913, 886, 716, 697, 661, 621, 582-cm. Atom analysis: C 43.65, H 6.889, S 5.90, Zn 11.76; calculating valuation: C 43.52, H 6.94, S 5.81, Zn 11.85; molecule formula: $C_{20}H_{26}O_5SZn.6H_2O$.

Example 7

1 g of $ZnSO_4.7H_2O$ was added into 20 ml water, 20 ml of hydrous solution containing 1.78 g of sulfodehydroabietic acid disodium salt was added with stirring. The stirring was continued at ~60° C. for 0.5 hours. The mixture was cooled down to room temperature, then filtered, washed with 50° C. water to neutrality, dried at 60° C. for 48 hours to give 1.02 g of object substance.

Mp.>300° C.; others, such as IR etc. were the same as those in Example 6.

Example 8

5 g of sulfodehydroabietic acid was added into 200 ml water, 5 g of $BiN_2O_4$ was added, the stirring was continued at 90° C. for 1 hour. The mixture was cooled down and filtered, dried at 60° C. for 60 hours to give 6.7 g of sulfodehydroabietic acid bismuth salt.

Mp.>300° C.; $IRV$ max (KBr): 3381, 3035, 2910, 2883, 1699, 1623, 1553, 1484, 1384, 1357, 1316, 1186, 1444, 1097, 1056, 1024, 1008, 975, 713, 697, 662, 624, 579$cm^{-1}$. molecule formula: $C_{20}H_{26}O_7SBi_2.10H_2O$. calculating valuation: Bi41.43%, $H_2O$ 17.86%, EDTA titerating Bi 41.13%, $H_2O$ 17.6%.

Example 9

5 g of sulfodehydroabietic acid was dissolved into 200 ml water, 6.23 g of $BiN_2O_6$ was added. The mixture was heated to 90–100° C., stirred for 1 hour, cooled down to 60° C., filtered, washed with water, 95% ethanol and diluted acid for several times. The precipitates were dried at 60° C. for 60 hours to give 7 g of sulfodehydroabietic acid bismuth salt.

Mp.>300° C. IRV max (Kbr): 3433, 3041, 2937, 2885, 1698, 1631, 1553, 1486, 1362, 1185, 1144, 1097, 1057, 1044, 1030, 1009, 977, 910, 580 $cm^{-1}$. Atom analysis: C36.76, H4.88, S5.14; EDTA titerating, Bi31.63; calculating valuation: C36.48, H5.05, S4.87, Bi: 31.73, molecule formula: $C_{20}H_{27}O_6SBi.3H_2O$, water test (TGA): 2.77.

The invention claimed is:

1. Salts of sulfodehydroabietic acid, wherein, said salts can be represented by general formula (1):

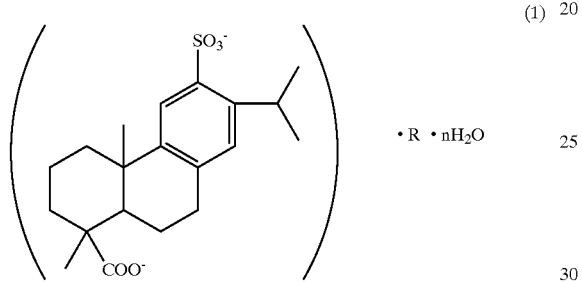

(1)

wherein, R is $Bi(OH)^{++}$, or $Zn^{++}$, or $2BiO^+$, $1/2ZnH$, n=0–10.

2. A method of preparing salts of sulfodehydroabietic acid with bismuth or zinc of claim 1, wherein said method comprises following steps:
   (1) Mixing rosin and lime hydrate in the ratio (wt) of 1:0.1–1:1.5, stirring at 160–600° C. for 1–5 hours, to obtain solid abietic acid calcium salt;
   (2) Dissolving said solid abietic acid calcium salt in $C_{1-6}$ fatty alcohol and $C_{1-6}$ fatty alcohol hydrous solution, or fatty acid ester, wherein the solvent used is 0.5–10 times as much as said solid abietic acid calcium salt, the unit ratio is ml/g; and adjusting pH value to 5–9 with mineral acid, so as to obtain abietic acid;
   (3) Incubating said abietic acid at 200–300° C. for 1–5 hours with the catalyst of 0.1–5% (wt) of 5%–10% palladium/carbon, or incubating directly at 220–380° C.; after incubation and cooling down, adding 0.5 to 10-fold (volume) solvent, said solvent can be any one of methanol, ethanol, propenol, acetyester acetic acid, benzene and methbenzene, keeping refluxed for 1–3 hours, filtering when it is warm, cooling down, allowing it to stand for overnight and be crystallized; dehydroabietic acid is obtained after filtering;
   (4) Adding said dehydroabietic acid into 1 to 10-fold (wt) 90–98% sulfuric acid pre-cooled to −2~20° C., after incubating for 0.5–10 hours with stirring, pouring it into ice cold water, wherein, said ice cold water is 5–50 times (wt) as much as said sulfuric acid; then, lots of white precipitation is crystallized out; filtering, washing the precipitates with water, and drying off; dissolving the precipitates into 0.5 to 10-fold (wt) glacier acetic acid with heating, allowing the mixture to be cooled down and be crystallized; the sulfodehydroabietic acid is obtained after filtered and dried off;

or, (5) Preparing single or double alkaline metal salts or alkaline earth metal salts of sulfodehydroabietic acid from said sulfodehydroabietic acid obtained with the conventional method;
   (6) Preparing the salts of sulfodehydroabietic acid with bismuth or zinc, namely the composition represented by formula (1), based on the displacement reaction of single or double alkaline metal salts or alkaline earth metal salts of sulfodehydroabietic acid obtained from the previous step with any one of zinc chloride, zinc sulfate, zinc nitrate, bismuth nitrate, bismuth subnitrate, and bismuth hydroxide in any one of solvents of $C_{1-6}$ fatty alcohol, water, DMF or DIMSO;

Or, (5)' Preparing the salts of sulfodehydroabietic acid with bismuth or zinc, namely the composition represented by formula (1), based on the neutralization reaction of sulfodehydroabietic acid obtained from the previous steps with any one of zinc chloride, zinc sulfate, zinc nitrate, bismuth nitrate, bismuth subnitrate, and bismuth hydroxide in any one of solvents of $C_{1-6}$ fatty alcohol, water, DMF or DIMSO.

3. A method for treating digestive canal ulcer and gastritis in a subject, comprising:
   administering to said subject an effective amount of said salts of sulfodehydroabietic acid of claim 1.

4. A pharmaceutical composition, includes said salts of sulfodehydroabietic acid of claim 1 and their pharmaceutical excipient.

5. The method of claim 3, wherein said subject is a mammal.

6. The method of claim 5, wherein said mammal is human.

7. The method of claim 3, wherein said salts are administered orally.

* * * * *